(12) United States Patent
Bauer et al.

(10) Patent No.: US 8,647,841 B2
(45) Date of Patent: Feb. 11, 2014

(54) ARTIFICIAL CHROMOSOME VECTOR

(75) Inventors: Anton Bauer, Kirchberg am Wagram (AT); Emilio Manuel Casanova Hevia, Vienna (AT); Leander Blaas, Vienna (AT)

(73) Assignees: Anton Bauer, Kirchberg am Wagram (AT); Emilio Casanova Hevia, Vienna (AT)

( * ) Notice: Subject to any disclaimer, the term of this patent is extended or adjusted under 35 U.S.C. 154(b) by 76 days.

(21) Appl. No.: 13/130,478

(22) PCT Filed: Nov. 18, 2009

(86) PCT No.: PCT/EP2009/065410
§ 371 (c)(1),
(2), (4) Date: May 26, 2011

(87) PCT Pub. No.: WO2010/060844
PCT Pub. Date: Jun. 3, 2010

(65) Prior Publication Data
US 2011/0229932 A1    Sep. 22, 2011

(30) Foreign Application Priority Data

Nov. 28, 2008   (AT) ................ A 1859/2008

(51) Int. Cl.
*C12P 21/06*   (2006.01)
*C12N 1/20*    (2006.01)
*C07H 21/02*   (2006.01)

(52) U.S. Cl.
USPC ....... 435/69.1; 435/325; 435/252.3; 536/23.1

(58) Field of Classification Search
USPC ................ 435/69.1, 325, 252.3; 536/23.1
See application file for complete search history.

(56) References Cited

U.S. PATENT DOCUMENTS 7,518,033 B2 * 4/2009 Seed et al. .............. 800/21
2008/0060093 A1  3/2008 Zieler et al.

FOREIGN PATENT DOCUMENTS

| WO | 02/096923 | 12/2002 |
| WO | 02/097059 | 12/2002 |
| WO | 2004/056986 | 7/2004 |

OTHER PUBLICATIONS

Moralli et al. (2006; A novel human artificial chromosome gene expression system using herpes simplex virus type 1 vectors. EMBO Reports7(9):911-918; Online Supplemental Information Only is provided.*
Lindenbaum et al. 2004; A mammalian artificial chromosome engineering system (ACE System) applicable to biopharmaceutical protein production, transgenesis and gene-based cell therapy. Nucleic Acids Research 32(21): e172 (which is 15 pages.*
Ferraro et al. 2007; Analysis of a quantitative trail locus for seizure susceptibility in mice using bacterial artificial chromosome-mediated gene transfer. Epilepsy. 48(9): 1667-1677.*
Blaas, L. et al., BMC Biotechnology, Biomed Central Ltd., 2009, vol. 9, No. 1, pp. 3.
Blaas, L., Musteanu, M., Zenz, R., Eferl, R. and Casanova, E., BioTechniques 43:659-660, 662, 664 (2007).
Felgenhauer, M., Kohl, J. and Ruker, F., "Nucleotide sequences of the cDNAs encording the V regions of H-and L-chains of human monoclonal antibody specific to HIV-1-gp41," Nucleic Acids Res., 18:4927 (1990).
Giraldo, P. and Montoliu, L., Transgenic Research, 10:83-103 (2001).
Hayflick, L., "The limited in vitro lifetime of human diploid cell strains," Exp. Cell Res. 37:614-636 (1965).
Huang, Y. et al., Journal of Immunological Methods 322:28-39 (2007).
Kwaks, T.H. et al., Nature Biotechnology, 21:553-558 (2003).
Moralli et al., EMBO Reports, 2006, 7:911-918.
Niwa, H., Yamamura, K. and Miyazaki, J., Gene, 108:193-199 (1991).
Tsyrulnyk, Andriy et al., Methods in Molecular Biology, 430:269-293 (2008).
Wurm, F.M., Nature Biotechnology, 22:1393-1398 (2004).
Austrian Patent App. No. A 1859/2008, Search Report of the Austrian Patent Office, Aug. 26, 2009.
International Preliminary Report on Patentability, International Patent Application No. PCT/EP2009/065410, Feb. 21, 2011.
International Search Report, International Patent Application No. PCT/EP2009/065410, Mar. 30, 2010.
Written Opinion of the International Searching Authority, International Patent Application No. PCT/EP2009/065410, Mar. 30, 2010.

* cited by examiner

*Primary Examiner* — Karen Cochrane Carlson
(74) *Attorney, Agent, or Firm* — Miachel Fedrick; Loza & Loza, LLP

(57) ABSTRACT

According to the present invention there is provided a method of producing a protein in a eukaryotic cell line, comprising the steps of a) providing a backbone of an artificial chromosome, b) recombining the nucleic acid encoding said protein into said backbone to generate an expression vector, c) introducing said expression vector into a eukaryotic host cell line to obtain a eukaryotic expression cell line, d) cultivating said expression cell line to produce said protein, and e) isolating said protein. The invention further relates to respective vectors and transgenic cell lines.

19 Claims, 4 Drawing Sheets

ARTIFICIAL CHROMOSOME VECTOR

CROSS-REFERENCE TO RELATED APPLICATIONS

Figure 1A:
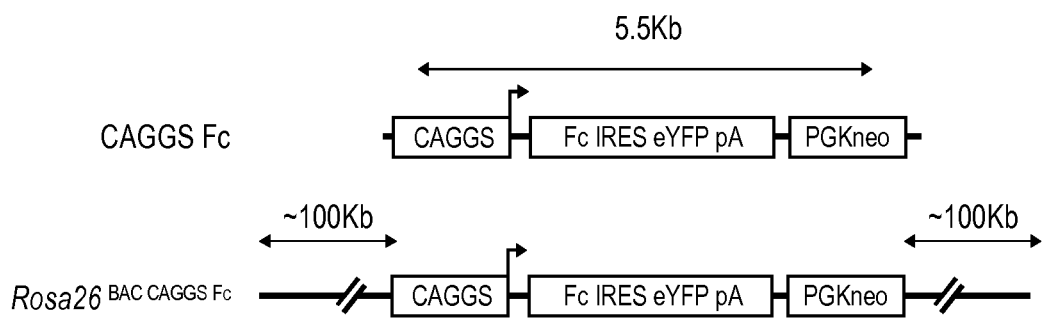

This application is the U.S. national stage of International Patent Application No. PCT/EP2009/065410, filed on Nov. 18, 2009 and entitled Artificial Chromosome Vector, which claims the benefit of priority from Austrian Patent Application No. A1859/2008, filed Nov. 28, 2008. The disclosures of the foregoing applications are incorporated herein by reference in their entirety.

SEQUENCE LISTING

The entire content of a Sequence Listing titled "Sequence_Listing.txt," created on May 16, 2011 and having a size of 1 kilobyte, which has been submitted in electronic form in connection with the present application, is hereby incorporated by reference herein in its entirety.

The invention refers to a method of producing proteins in mammalian host cell lines.

Recombinant protein production in mammalian cell systems is an important topic in biotechnology. One of the critical steps in the production of recombinant proteins is the generation of cell lines expressing high levels of the protein of interest and the isolation of single cell clones thereof with stable expression over cell-division cycles and time (Wurm, F. M. Nature Biotechnology 22, 1393-1398 (2004)). There is a need for methods generating cell lines stably, safely, reliably and reproducibly expressing high yields of secreted proteins in cell culture on the industrial scale. This need is particularly increasing with the increasing amount of biologicals developed and produced for therapy by the pharmaceutical industry.

Commonly, this is achieved by random genomic integration of an expression vector containing a promoter, a gene of interest and a selectable marker into the chromosomal DNA of established production cell lines.

Frequently used production cell lines are derived from mammal or insect cells. A cell line is a permanently established cell culture that will proliferate indefinitely given appropriate fresh medium and space. Cell lines differ from cell strains in that they have escaped the Hayflick limit (Hayflick L. (1965). "The limited in vitro lifetime of human diploid cell strains." *Exp. Cell Res.* 37 (3): 614-636) and become immortalised. Examples for established production cell lines are CHO, NSO, COS, or Sf9 cells, or human cell lines like PerC-6 and HEK293, For genetic engineering of mammalian cells as well as cell lines usually plasmids are used as vectors. A plasmid is a non-chromosomal DNA molecule separate from the chromosomal DNA, which is capable of replicating independently of the chromosomal DNA in bacteria. In many cases, it is circular and double-stranded. In proliferating mammalian cells, the plasmid can be maintained indefinitely in host cells after random integration into the genome of the host cell, and can lead to production of the gene/product of interest, commonly a protein, via its promoter.

Although this method of genetic engineering is simple and straight forward, it lacks reproducibility. Expression of proteins from such vectors is substantially influenced by the chromatin surrounding the integration site, which tends to silence expression over time (Wurm, F. M. Nature Biotechnology 22, 1393-1398 (2004)). This makes the selection of suitable clones a tedious and time consuming procedure.

Several strategies have been developed to overcome the positional effects of the adjacent chromatin. For example, "anti-repressor" elements flanking the vectors have been used or vectors have been integrated specifically into chromosomal loci with open chromatin (Kwaks, T. H. et al. Nature Biotechnology 21, 553-558 (2003), Huang, Y. et al. Journal of Immunological Methods 322, 28-39 (2007)).

Artificial chromosomes have been used in the art to provide for transgenic hosts, such as animals or plants.

WO2002/097059A2 describes artificial chromosomes that have been engineered to contain available sites for site-specific, recombination-directed integration of DNA, particularly useful for engineering transgenic animals.

US2008/0060093A1 discloses methods of generating plants transformed with autonomous mini-chromosomes.

Moralli et al (EMBO reports 2006 Vol 7(9) 911-918) disclose human artificial chromosome (HAC) vectors to be used as a gene transfer system for expression and complementation studies.

The development of appropriate protein expression vectors constitutes one critical step in recombinant protein production in eukaryotic cell lines. For recombinant protein production in cell culture, generally a vector is sought that displays the following features:

1) expression should be independent of the integration site in the genome,
2) expression should correlate with the number of integrated transgene copies,
3) expression should be maintained over time, and
4) the expression level should be high.

It is the object of the present invention to provide a method and a vector that allows the generation of stable cell clones to improve recombinant protein production in eukaryotic production cell lines.

The object has been solved by the subject matter of the present invention.

According to the present invention there is provided a method of producing a protein in a eukaryotic cell line, comprising the steps of a) providing a backbone of an artificial chromosome,
b) recombining the nucleic acid encoding said protein into said backbone to generate an expression vector,
c) introducing said expression vector into a eukaryotic host cell line to obtain a eukaryotic expression cell line,
d) cultivating said expression cell line to produce said protein, and
e) isolating said protein.

Thus, the expression cell line as used according to the invention has an integrated expression vector based on an artificial chromosome.

The cell line as used according to the invention is understood as a permanently established cell culture that will proliferate indefinitely given appropriate fresh medium and space, thus has been immortalized. Hereinafter the cell line as used according to the invention is also called "host cell line" or "host cell".

The method according to the invention in particular refers to artificial chromosome constructs containing foreign nucleic acid sequences and methods of using these constructs for ex vivo production of proteins, like secretion proteins.

According to the invention artificial chromosomes may be used in production cell lines for large scale production of recombinant proteins. The artificial chromosomes preferably are derived from bacteria, like a bacterial artificial chromosome, also called "BAC", e.g. having elements from the F-plasmid, or artificial chromosome with elements from the P1-plasmid, which are called "PAC". Artificial chromosomes can also have elements from bacteriophages, like in the case of "cosmids". Further artificial chromosomes preferably as used according to the invention are derived from yeast, like a yeast artificial chromosome, also called "YAC", and from mammals, like a mammalian artificial chromosome, also called "MAC", such as from humans and a human artificial chromosome, called "HAC".

These artificial chromosomes have in common, that they contain replication origin sequences needed for replication and preservation over cell divisions in the respective cell used for DNA amplification. Cosmids, BACs, and PACs have replication origins from bacteria, YACs have replication origins from yeast, MACs have replication origins of mammalian cells, and HACs have replication origins of human cells. In addition, the artificial chromosomes as used according to the invention may have selection markers, usually antibiotic resistance, which allows the selection of cells carrying an artificial chromosome.

These artificial chromosomes are vectors including elements derived from chromosomes that are responsible for replication and maintenance in the respective organism, and are capable of stably maintaining large genomic DNA fragments. These large genomic DNA fragments are usually in the range of 30-50 kb for cosmids, 50-350 kb for PACs and BACs, 100-3000 kb for YACs, and >1000 kb for MACs and HACs.

According to a preferred embodiment, the artificial chromosome as used according to the invention is selected from the group consisting of BAC, YAC, PAC and cosmids, which group is also called "microbial artificial chromosomes". The microbial artificial chromosomes usually are small chromosomes of 5000 kbp at the maximum. The size of an artificial chromosome according to the invention preferably is 100-350 kbp, but can also be greater than 350 kbp.

The preferred artificial chromosome backbones as used according to the invention are of bacterial, bacteriophage or yeast origin. These can be considered together as microbial artificial chromosomes with very similar vector features but different capacity for inserted DNA loci. Besides, the artificial chromosomes derived from BAC, cosmid, PAC, YAC, likewise, those from mammals (MAC) or human (HAC) may be used. As a BAC backbone the Rosa26BAC construct is preferably used according to the invention. Also other loci considered as open chromatine, such as b-actin, Gapdh, Hprt, ribosomal proteins may be used.

Additional elements of an artificial chromosome as used according to the invention are elements of the large fragments of DNA containing gene loci. These gene loci are preferred and functional after the artificial chromosomes have been introduced into the respective eukaryotic production cell lines. These gene loci contain elements regulating the chromatin structure and accessibility to transcription factors, and elements determining the transcription levels, like enhancer and promoter sequences, for the expression of gene-products of interest.

In an artificial chromosome, some of these before-mentioned elements are only required for proper amplification of DNA. These elements are the origin of replications and a marker gene for selection in e.g. bacteria and yeast, like antbiotic resistance. Thus, the part of the artificial chromosome carrying these elements is called the backbone.

Artificial chromosomes are large, DNA-based vectors that have been used extensively in the construction of DNA libraries for complex genome mapping and analysis. BACs have been used to sequence the genome of organisms in large scale sequencing projects, for example the Human Genome Project. A short piece of the organism's DNA is amplified as an insert in BACs, and then sequenced. Finally, the sequenced parts are rearranged in silico, resulting in the genomic sequence of the organism.

BACs have also been used as large vectors for generation of transgenic mice (Giraldo, P. & Montoliu, L. Transgenic research 10, 83-103 (2001). In this example, primary cells of the mice express the gene of interest regulated via the respective locus in the BAC.

It turned out that artificial chromosomes could be used in the production of eukaryotic expression cell lines having improved properties. For example, it has surprisingly been demonstrated that a BAC based vector according to the present invention can be applied to transfect eukaryotic cell lines and to express recombinant proteins in cell lines in cell culture in a highly efficient way. According to a preferred embodiment of the invention, a BAC based vector according to the invention was used to produce a fragment of the constant region of the human IgG1. Direct comparison of bulk HEK 293 cell cultures generated with a conventional vector or with a BAC-based vector showed that the BAC-based vector surprisingly improved the protein yield by a factor of 10. Further analysis of stable cell clones harbouring the BAC-based vector showed that the protein production was directly proportional to the number of integrated BAC copies and that the protein production was stable even after 30 passages.

According to the invention it is thus possible to improve the expression of secretion proteins and polypeptides in general, in particular for the purpose of industrial production of recombinant proteins, which usually involves the production on a large scale, e.g. using at least 1 liter fermentation volume, more preferred at least 5 liter, even more preferred fermentation is carried out using at least 100 liter fermentation broth. Fermentation is preferably employed using batch or continuous fermentation techniques.

Secretion proteins are proteins or polypeptides that are produced and secreted from a eukaryotic host cell to its extracellular environment. Usually this is supported by signal peptides, which are understood as a short, e.g. 2-100 amino acids long, peptide sequence that directs the post-translational transport of a protein. Signal peptides are generally used for producing proteins secreted from the production cells. These signal peptides are usually cleaved off to form a mature secreted protein. Example for a signal peptide leading to a secreted protein is "MELGLSWIFLLAILKGVQC" found for human kappa light chain (Felgenhauer, M., Kohl, J. and Ruker, F; Nucleotide sequences of the cDNAs encoding the V-regions of H- and L-chains of a human monoclonal antibody specific to HIV-1-gp41; Nucleic Acids Res. 18 (16), 4927 (1990)). Signal peptides may also be called targeting signals, signal sequences, transit peptides, or localization signals.

The amino acid sequences of signal peptides direct proteins (which are synthesized in the cytoplasm) to certain organelles such as the nucleus, mitochondrial matrix, endoplasmic reticulum, chloroplast, apoplast and peroxisome. Signal peptides used in expression vectors are usually cleaved from the protein by signal peptidase after the proteins are transported.

The vector according to the invention is thus based on an artificial chromosome including a gene that may encode a secretion protein, preferably employing a signal peptide, e.g. in conjunction with the secretion protein. The signal peptide is preferably cleaved from the secretion protein upon expression and transport into the cell culture supernatant.

The method according to the invention is preferably used to provide recombinant proteins selected from the group consisting of serum proteins, including immunoglobulins, immunoglobulin fragments or derivatives, albumin, blood factors, polypeptide hormones, cytokines, chemokines, enzymes and growth factors, and derivatives thereof.

A derivative includes any fragment, conjugate, fusion, nucleic acid or homologue of a polypeptide, which is originating from or similar to the secretion protein.

In order to produce the protein according to the invention, the expression cell line is cultivated to produce the protein, and the protein is isolated. Therefore, methods of isolation or separation as used in the art may be employed, such as chromatographic separation methods to quantitatively isolate the product.

As a eukaryotic host cell any host cell is used that may provide for eukaryotic protein glycosylation, if necessary. Preferably mammalian or insect single cell or cell line of human, primates, mouse, hamster cells are used. Preferred examples are HEK cells, such as HEK293, CHO, COS, NSO cells, mouse lymphoblast cells, PerC6, or Sf9 cells.

The nucleic acid encoding said recombinant proteins is preferably recombined with the artificial chromosome backbone gene by recombination techniques, such as homologous recombination or cassette exchange, such as mediated by integrase, like φC31 integrase mediated cassette exchange.

The vector according to the invention is preferably stably integrated into the chromosome of the host cell, preferably a mammalian or insect chromosome, more preferably a chromosome of human, murine or hamster origin, to provide a transgenic host.

The transgenic cell line according to the invention is provided either as a single cell, stable single cell clone, as a cell line or the like. However, the invention explicitly excludes transgenic humans. Preferably the transgenic host cell is harboring the vector within the genetic map of its chromosome, usually in conjunction with or directly linked in a locus of an abundantly expressed gene or protein, also called abundant protein.

An abundant protein as understood herein is a protein that is highly expressed at the level of mRNA and polypeptide by the host cell, e.g. ribosomal proteins, cytoskeleton proteins and proteins for DNA synthesis, like DNA polymerase. Such an abundant protein is usually a native protein that is highly expressed by the host cell. Using the locus of an abundant protein usually facilitates the stable expression of the artificial chromosome encoded secretion protein at a high rate. Again it is preferred that the locus is of mammalian or insect origin.

The selected locus preferably contains regulatory elements for open chromatin formation or protein expression in general. In particular it is preferred that an anti-condensation enhancer is employed, either through an element that is contained in the locus as a native enhancer, or through an exogenous, heterologous or synthetic regulatory element that provides for the expression chromatin structure. Thereby the locus is accessible to transcription factors.

The "open chromatin" or "active chromatin" or "euchromatin" region can be subject to structural changes, resulting in less condensed and highly transcribed structures. The formation of euchromatin is believed to represent the underlying mechanism of chromatin-mediated gene regulation, keeping genes in an active state, which is preferable to obtain a vector based on an artificial chromosome, which is designed for protein expression.

In the fields of genetics and evolutionary computation, a locus is understood as a fixed position on a chromosome that may be occupied by one or more genes. A locus of a protein is understood as a gene position that is dedicated for expressing at least part of said protein. A variant of the DNA sequence at a given locus is called transgenic chromosome. The ordered list of loci known for a particular genome is called a genetic map.

Preferably the locus as used according to the invention is derived from the sequences of the production cell line. For example, for a mammalian host, a locus of mammalian proteins, also called mammalian locus is used. For an insect cell, a locus of an insect protein is preferably used, also called insect locus. Preferably human or murine loci are employed according to the invention. Exemplary loci are Rosa 26 or loci of abundantly expressed and essential genes, like beta-actin and other proteins of the cytoskeleton as well as ribosomal proteins.

It is even more preferred to employ loci of the same type or species as the host cell, which provides for an allogenic locus. For example, a mammalian locus is integrated into the vector for mammalian host cell production, e.g. a human locus integrated into a vector according to the invention is introduced into a human cell line. This allogenic system is preferably used for the production of human proteins. It is further preferred that a vector with a mouse locus is preferably integrated into a murine host cell line, and a vector with a hamster locus is preferably integrated into a hamster host cell line and a vector with an insect locus is integrated in an insect cell line.

Regulatory elements as used according to the invention include preferably a promoter, either a native promoter, which is contained in the native locus, or as a heterologous element, such as eukaryotic and/or prokaryotic promoters, or even dual promoters may be used. Exemplary promoters are generic ones, preferably CMV, Caggs, Tk (timidine kinase), ubiquitin C or EF2, which are commonly used for transfection. Besides the artificial promoters also natural promoters like beta-actin or ribosomal proteins can be used. Preferably a strong promoter is selected.

It has been proven that it is preferred to introduce more than one copy of the artificial chromosome into the host cell to improve the yield, preferably at least 2 copies, more preferably at least 3 copies, more preferably at least 5 or 10 copies, up to 50 copies may be preferably integrated into the host cell. It may however be advantageous to employ even a higher number of artificial chromosomes, up to 500 copies, in particular when more than one locus is employed to express the protein. The increased number of integrated copies of the artificial chromosome in the genome directly correlates with increased expression of the gene of interested and thus increased yield of the respective encoded protein. This is a clear improvement compared to the use of knock-in strategies, where the gene of interest is inserted into one or two copies of a chromosomal locus of a host cell line without the use of artificial chromosomes.

Thus, the use of artificial chromosome according to the invention supports a high yield of protein expression. The production method according to the invention preferably provides for yields of at least 1 pg/cell/day, preferably at least 3, 5, 10, 30, 50 up to 100 pg/cell/day. The yields may be improved upon increasing the density of said host cells by appropriate amplification.

It turned out that the clone according to the invention is stably producing the protein, even after multiple passaging. It has surprisingly been shown that the yield is not significantly reduced, i.e. by no more than 30%, even after passage 10, 20 or 30, thus demonstrating a stable expression system.

The vector according to the invention may be provided as an expression tool to facilitate recombinant protein production combined with conventional expression units, or preferably as a complete expression unit on its own. Thus, it is preferred that the vector according to the invention harbors regulatory elements of a gene to enable random integration of the artificial chromosome in stable cell lines, without affection by surrounding chromatin.

In a specific embodiment, the vector according to the invention is provided as complete expression unit containing all regulatory elements to provide for stable protein expression. Thus, the vector according to the invention may be introduced into the host cell independent of the chromosomal integration.

It turned out, that for example, a BAC-based vector according to the invention offers a clear advantage compared with a conventional vector. It provides higher levels of expression, e.g. at least 10 times, and it is less affected by undesirable chromatin effects, thus simplifying the isolation of single cell clones expressing high levels of the protein of interest. Furthermore, vectors based on artificial chromosomes can make use of endogenous regulatory elements, thus avoiding silencing of the expression in long-term cultures.

The use of vectors based on artificial chromosomes according to the invention, in particular the small artificial chromosomes, like microbial artificial chromosomes, e.g. BAC, offers all the advantages of knock-in strategies. In addition, those vectors can be integrated in the host genome with a high copy number, while knock-in vectors are integrated as 1 or two copies at most. The expression of the vectors is proportional to the number of integrated copies, thus a vector based on artificial chromosomes offers higher expression levels than a knock-in strategy, Furthermore, generation of stable cell lines according to the invention, in particular using BAC-based vectors, is a simple process and less time-consuming than knock-in strategies. As mentioned above, expression of gene of interest using conventional vectors is highly subjected to undesirable chromatin effects. To overcome this problem, conventional vectors are flanked by short DNA sequences called chromatin isolators. There is a long list of DNA elements considered chromatin isolators, e.g. locus control regions, matrix attachments elements, antirepressor elements, ubiquitous chromatin elements, boundary elements, etc. (Wurm, F. M. Nature Biotechnology 22, 1393-1398 (2004)). All these elements have been used in conventional vectors with variable success rates. These chromatin isolators are short DNA sequences used out of their real genomic context, thus not providing a true chromatin environment.

On the other hand, vectors based on artificial chromosomes as used according to the invention containing a particular locus (vg Rosa 26) are by definition a chromatin unit. They contain most, if not all the chromatin regulatory elements of a defined locus in the real endogenous genomic context. Thus, the vectors as used according to the invention provide a much better chromatin regulation or environment than conventional vectors flanked only with chromatin isolators. According to a preferred embodiment, the method according to the invention does not make use of chromatin isolators.

FIG. 1A shows a schematic representation of the constructs used for protein production. CAGGS Fc is a conventional expression vector containing a CAGGS promoter, a signal peptide followed by the Fc region of the IgG1 gene, an IRES-eYFP-SV40 polyA reporter element and a PGK neomycin cassette. The Rosa26$^{BAC\ CAGGS\ Fc}$ construct was generated by recombining the CAGGS Fc vector into a BAC containing the Rosa26 locus. The CAGGS Fc vector was placed into the exon 2 of antisense transcript of the Rosa26 locus with 100 kb upstream and downstream sequence.

Figure 1B:
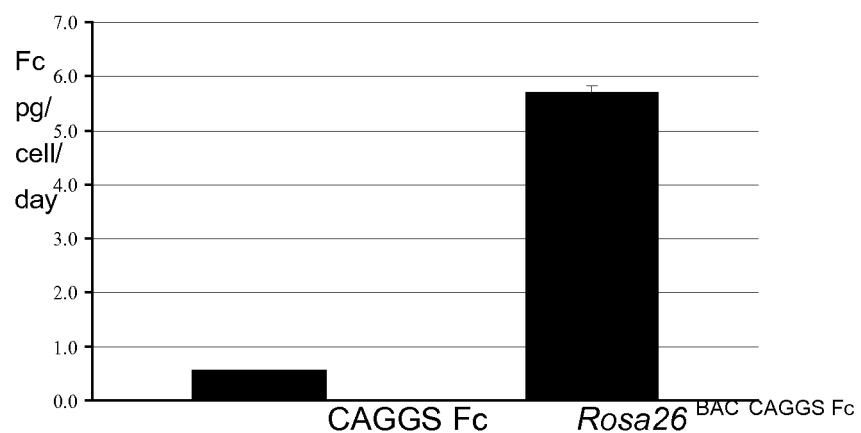

FIG. 1B shows a comparison of the efficacy in protein production between a conventional vector and a BAC-based vector. The Fc yield was analyzed in HEK 293 bulk cultures (cell pools) generated with the CAGGS Fc and Rosa26$^{BAC\ CAGGS\ Fc}$ vectors. The CAGGS Fc vector gave a yield of 0.5 pg/cell/day, while the BAC-based vector gave a yield of 5.7 pg/cell/day. Measurements were performed in triplicates. The error bars indicate the standard deviation.

Figure 1C:
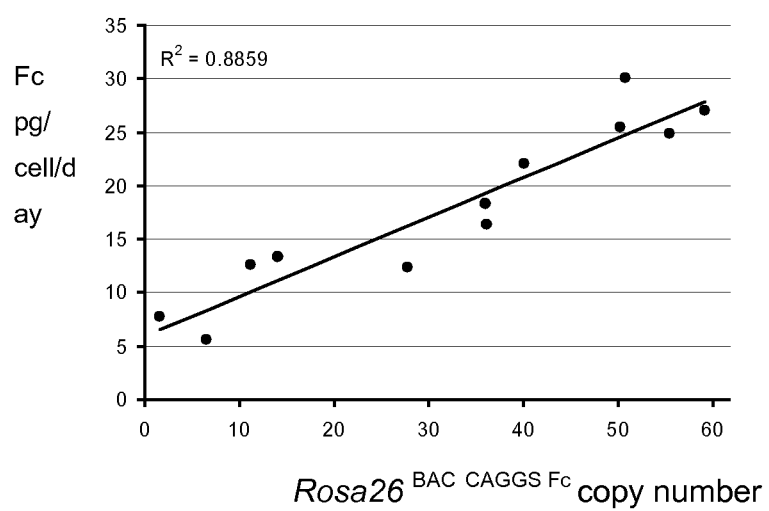

FIG. 1C shows a correlation between protein production and integrated BAC transgene copies. Analysis of 12 single clones showed a copy number range from 1 to 55 for the Rosa26$^{BAC\ CAGGS\ Fc}$ vector with a Fc yield of 5.5 to 30 pg/cell/day. The protein production was directly proportional to the BAC transgene copy number.

Figure 1D:
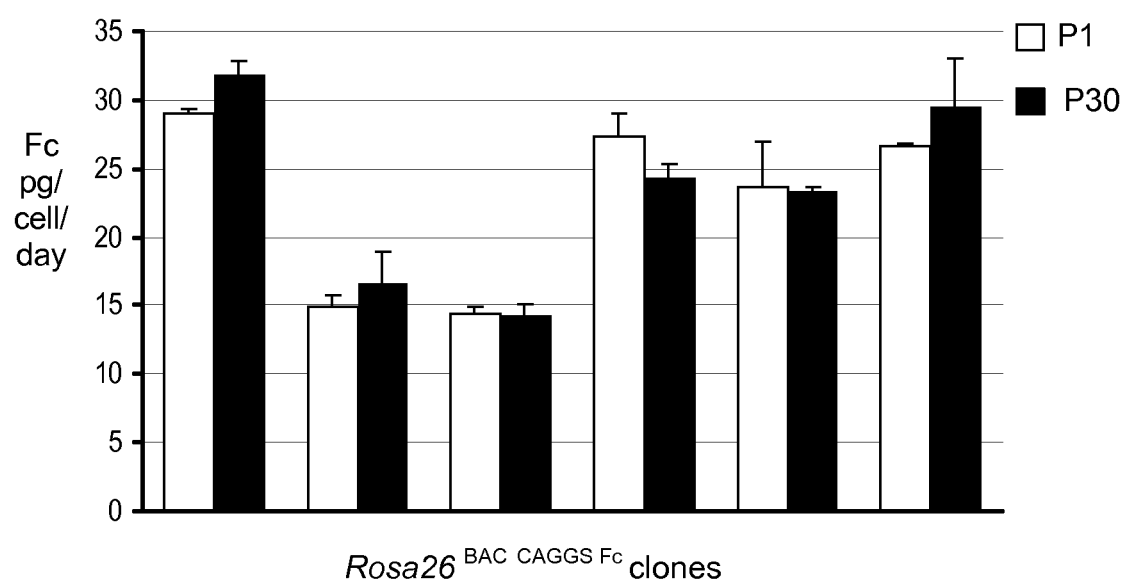

FIG. 1D shows that the protein production is stably maintained during culture passaging. The yield of Fc protein was measured at passage 1 and passage 30 in 6 subclones isolated from the Rosa26$^{BAC\ CAGGS\ Fc}$ cultures. No obvious differences were found. The error bars indicate the standard deviation.

The invention is further described by means of the following examples.

EXAMPLE 1

Expression of Human Fc

In order to test the efficacy of BACs in the production of recombinant proteins, we have generated two expression vectors: The CAGGS Fc vector, which consists of a CAGGS promoter (Niwa, H., Yamamura, K. & Miyazaki, J. *Gene* 108, 193-199 (1991)), a signal peptide followed by the Fc fragment (i.e. hinge, $C_H2$ and $C_H3$) of human IgG1 as gene of interest (Fc), an IRES/eYFP reporter and a PGK-neomycin cassette. The second vector, Rosa26$^{BAC\ CAGGS\ Fc}$, consists of the CAGGS Fc vector that has been recombined into a BAC backbone containing the Rosa26 locus (FIG. 1A).

HEK 293 cells were transfected with the CAGGS Fc and the Rosa26$^{BAC\ CAGGS\ Fc}$ vectors. After 14 days of G418 selection, two bulk cultures (cell pools) for the CAGGS Fc and Rosa26$^{BAC\ CAGGS\ Fc}$ were established. Analysis of the Fc protein production in the supernatants showed a yield of 0.5 and 5.7 pg/cell/day in the CAGGS Fc and the Rosa26$^{BAC\ CAGGS\ Fc}$ bulk (cell pools) cultures, respectively (FIG. 1B), demonstrating that the use of a BAC-based vector improves the protein production substantially. Next, we analyzed the correlation between the number of transgene copies and the Fc protein yield. 12 subclones were established from the of Rosa26$^{BAC\ CAGGS\ Fc}$ culture that harbored 1 to 55 copies of the transgene. Protein yield in the supernatants of these cultures correlated with the transgene copy numbers and ranged from 5.5 to 30 pg/cell/day (FIG. 1C). The correlation coefficient $R^2$ between the copy number of the BAC vector and protein production was 0.88. This suggests that the protein production is proportional to the number of integrated transgene copies when using a BAC-based expression vector.

Finally, we investigated long-term protein production over time and increasing passage numbers. 6 subclones from the Rosa26$^{BAC\ CAGGS\ Fc}$ culture were grown for 30 passages and protein production was analysed. The yield of the Fc protein was not significantly decreasing from passage 1 to passage 30 (FIG. 1D) indicating that BAC-based vectors provide stable production of recombinant protein over time.

In this work, we have used a BAC containing the Rosa26 locus to shield an expression unit (the CAGGS Fc). With this approach, we have shown that a BAC-based vector yields better results than conventional vectors for recombinant protein production. Further improvements of BAC-based vectors for recombinant protein production may include the use of endogenous/natural promoters that are highly active in the producer cell. For example, a transcriptional profiling of HEK 293 cells has identified strong expression levels of the Rpl23a gene which encodes a ribosomal protein. Therefore, the use of a BAC containing the Rpl23a locus in HEK 293 cells may further improve recombinant protein production.

Materials and Methods

Plasmids and Cell Culture

The CAGGS Fc expression vector was assembled by conventional cloning methods and is flanked by two attB sites (phiC31 integrase recognition sites). The Rosa26$^{BAC\ CAGGS}$ $_{Fc}$ BAC vector was generated as previously described (Blaas, L., Musteanu, M., Zenz, R., Eferl, R. & Casanova, E. *BioTechniques* 43, 659-660, 662, 664 (2007)). Briefly, the CAGGS Fc vector was recombined into a BAC containing the Rosa26 locus using phiC311 mediated cassette exchange into the exon 2 of the Rosa26 antisense transcript.

To establish the bulk cultures, 24 μg CAGGS Fc and Rosa26$^{BAC\ CAGGS\ Fc}$ BAC vectors were linearized with NotI and transfected into HEK 293 using Lipofectamine 2000 (Invitrogen). Two days after transfection, G418 (800 μg/ml) was added to the media (DMEM high glucose, 10% FCS, supplemented with glutamine, pyruvate and non essential aminoacids). Selection was carried out over 14 days. Thereafter, cultures were grown in the absence of G418 and Fc protein production in the bulk cultures was measured 1 week later.

The Fc protein could be isolated using chromatographic methods.

Fc Protein Determination $5\times10^5$ cells were seeded into each single well of a 6 well plate in 2 ml of medium. 72 hours after seeding, the Fc protein concentration was measured in the supernatants using an ELISA assay. For the ELISA, goat anti-human-IgG (Fc specific) F(ab')2 fragment (Sigma 1-3391) was adsorbed at 1 μg/ml onto microwells of a Maxisorp plate over night at 4° C., followed by blocking with 5% BSA in PBS for 1 h at 25° C. After washing, the samples and the standard, respectively, were added in dilution series to the blocked microwells and incubated for 1 h at 25° C. The plate was washed and bound Fc was detected by Protein A—HRP (SIGMA P-8651) diluted 1:70000 in PBS/BSA followed by staining with TMB substrate solution (Sigma T0446). The ELISA was measured at 450 nm with the reference wavelength 630 nm.

Rosa26$^{BAC\ CAGGS\ Fc}$ Copy Number Analysis

Stable subclones from the Rosa26$^{BAC\ CAGGS\ Fc}$ culture were established using eYFP FACS sorting. The number of transgene copies in the single cell clones was quantified by real time PCR with genomic DNA as template. The Rosa26 BAC was amplified with oligos RosaF 5' TCTTGTCCTTT-TACCTCCCTTGTA (SEQ ID No. 1) RosaR 5' GAACATAT-TCAAAACACCAGGATTT (SEQ ID No. 2). These oligos recognize the BAC and the endogenous ROSA26 locus. The beta-actin locus was amplified with oligos, actinF 5' TCAT-GTTTGAGACCTTCAACACC (SEQ ID No. 3) and actinR 5' GATCTTCATGAGGTAGTCAGTCAGGT (SEQ ID No. 4) as internal control.

The invention claimed is:

1. A method of producing a protein in a eukaryotic production cell line, comprising the steps of:
   a) providing a backbone of an artificial chromosome which comprises a functional gene locus,
   b) recombining a nucleic acid encoding said protein into said backbone to generate an artificial chromosome expression vector,
   c) linearizing and randomly introducing said expression vector into a eukaryotic host cell line to obtain a eukaryotic expression cell line, wherein at least 5 copies of the artificial chromosome are stably integrated into the chromosome of the host cell,
   d) cultivating said expression cell line to produce said protein, and
   e) isolating said protein.

2. The method according to claim 1, wherein said recombining is performed using a method selected from the group consisting of homologous recombination and integrase mediated cassette exchange.

3. The method according to claim 1 wherein the number of copies of said expression vector that are stably integrated into said host cell line is in the range of 10 to 500.

4. The method according to claim 1, wherein a secretion protein is produced.

5. The method according to claim 4, wherein said secretion protein includes a signal peptide.

6. The method according to claim 4, wherein said secretion protein is a serum protein.

7. The method according claim 6, wherein said serum protein is selected from the group consisting of immunoglobulins, immunoglobulin fragments or derivatives, albumin, blood factors, polypeptide hormones, cytokines, chemokines, enzymes, growth factors, and derivatives thereof.

8. The method according to claim 1, wherein said artificial chromosome is derived from a bacterium, a bacteriophage, a yeast or a mammal.

9. The method according to claim 8, wherein said artificial chromosome is selected from the group consisting of a BAC, a PAC, a YAC and a cosmid.

10. The method according to claim 9, wherein said artificial chromosome is a BAC.

11. The method according to claim 1, wherein said vector contains a regulatory element for open chromatin formation.

12. The method according to claim 1, wherein said vector contains a native or heterologous promoter.

13. The method according to claim 1, wherein said vector contains a locus of an abundant protein selected from the group consisting of ribosomal proteins, cytoskeleton proteins and proteins for DNA synthesis.

14. The method according to clam 13, wherein said locus is the Rosa26 locus.

15. The method according to claim 1, wherein said vector contains a locus of mammalian or insect origin.

16. The method according to claim 1, wherein the number of copies of the expression vector that are stably integrated into said host cell line is between 5 and 55.

17. A transgenic production cell line produced by a method comprising the steps of:
   a) providing a backbone of an artificial chromosome which comprises a functional gene locus;
   b) recombining a nucleic acid encoding a protein into said backbone to generate an artificial chromosome expression vector, the expression vector further comprising an allogenic locus; and
   c) linearizing and randomly introducing the expression vector into a eukaryotic host cell line to obtain a eukaryotic expression cell line, wherein at least 5 copies of the artificial chromosome are stably integrated into the chromosome of the host cell.

18. The cell line of claim 17, wherein between 10 and 55 copies of the artificial chromosome are stably integrated into the chromosome of the host cell.

19. The cell line of claim 17, wherein the artificial chromosome is a BAC and the locus is Rosa26.

* * * * *

SEQUENCE LISTING

```
<160> NUMBER OF SEQ ID NOS: 4

<210> SEQ ID NO 1
<211> LENGTH: 24
<212> TYPE: DNA
<213> ORGANISM: artificial
<220> FEATURE:
<223> OTHER INFORMATION: amplification oligo "RosaF"

<400> SEQUENCE: 1
tcttgtcctt ttacctccct tgta                                        24

<210> SEQ ID NO 2
<211> LENGTH: 25
<212> TYPE: DNA
<213> ORGANISM: artificial
<220> FEATURE:
<223> OTHER INFORMATION: amplification oligo "RosaR"

<400> SEQUENCE: 2
gaacatattc aaaacaccag gattt                                       25

<210> SEQ ID NO 3
<211> LENGTH: 23
<212> TYPE: DNA
<213> ORGANISM: artificial
<220> FEATURE:
<223> OTHER INFORMATION: amplification oligo "actinF"

<400> SEQUENCE: 3
tcatgtttga gaccttcaac acc                                         23

<210> SEQ ID NO 4
<211> LENGTH: 26
<212> TYPE: DNA
```

```
<213> ORGANISM: artificial
<220> FEATURE:
<223> OTHER INFORMATION: amplification oligo "actinR"

<400> SEQUENCE: 4
gatcttcatg aggtagtcag tcaggt                                          26
```